US011083585B2

(12) United States Patent
Servidio

(10) Patent No.: US 11,083,585 B2
(45) Date of Patent: Aug. 10, 2021

(54) SPRING RETAINED FEMORAL AUGMENT

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 90 days.

(21) Appl. No.: 16/407,555

(22) Filed: May 9, 2019

(65) Prior Publication Data

US 2020/0352724 A1 Nov. 12, 2020

(51) Int. Cl.
*A61F 2/30* (2006.01)
*A61F 2/38* (2006.01)

(52) U.S. Cl.
CPC ........ *A61F 2/30734* (2013.01); *A61F 2/3859* (2013.01); *A61F 2002/3069* (2013.01); *A61F 2002/30131* (2013.01); *A61F 2002/30133* (2013.01); *A61F 2002/30266* (2013.01); *A61F 2002/30505* (2013.01); *A61F 2002/30736* (2013.01)

(58) Field of Classification Search
CPC ................ A61F 2/30734; A61F 2/3859; A61F 2002/30736; A61F 2002/30505; A61F 2002/30131; A61F 2002/30133; A61F 2002/30266; A61F 2002/3069
See application file for complete search history.

(56) References Cited

U.S. PATENT DOCUMENTS

| | | |
|---|---|---|
| 4,731,086 A | 3/1988 | Whiteside et al. |
| 4,936,847 A | 6/1990 | Manginelli |
| 5,080,674 A | 1/1992 | Jacobs et al. |
| 5,370,693 A | 12/1994 | Kelman et al. |
| 5,387,241 A | 2/1995 | Hayes |
| 5,458,637 A | 10/1995 | Hayes |
| 5,549,685 A | 8/1996 | Hayes |
| 5,571,194 A | 11/1996 | Gabriel |
| 5,609,645 A | 3/1997 | Vinciguerra |
| 5,702,460 A | 12/1997 | Carls et al. |
| 5,755,800 A | 5/1998 | O'Neil et al. |
| 5,766,255 A | 6/1998 | Slamin et al. |
| 5,938,698 A | 8/1999 | Sandoz et al. |
| 5,984,969 A | 11/1999 | Matthews et al. |
| 6,005,018 A | 12/1999 | Cicierega et al. |
| 6,074,424 A | 6/2000 | Perrone, Jr. et al. |

(Continued)

FOREIGN PATENT DOCUMENTS

| | | | |
|---|---|---|---|
| DE | 102016223289 A1 | 5/2018 | |
| FR | 2740327 A1 | 4/1997 | |

(Continued)

*Primary Examiner* — Dinah Baria

(74) *Attorney, Agent, or Firm* — Lerner, David, Littenberg, Krumholz & Mentlik, LLP

(57) ABSTRACT

An orthopedic system that includes a first augment that has a body and a first biasing member projecting from the body. The body has a first and second face. The first and second faces are separated by a thickness of the augment. The system also includes a femoral prosthesis that has an articular side that defines condylar portions and a bone-facing side opposite the articular side. The bone facing side defines an augment opening that is sized to receive the augment therein. When the first augment is received within the augment opening, the first biasing member presses directly against the femoral prosthesis so as to retain the body within the augment opening.

18 Claims, 7 Drawing Sheets

(56) References Cited

U.S. PATENT DOCUMENTS

| | | |
|---|---|---|
| 6,387,131 B1 | 5/2002 | Miehlke et al. |
| 6,896,702 B2 | 5/2005 | Collazo |
| 7,547,327 B2 | 6/2009 | Collazo |
| 8,632,599 B1 | 1/2014 | Bonitati et al. |
| 8,828,089 B1 | 9/2014 | Perez et al. |
| 9,089,430 B2 | 7/2015 | Pappas et al. |
| 9,162,008 B2 | 10/2015 | Serafin, Jr. et al. |
| 9,241,800 B2 | 1/2016 | Gustilo et al. |
| 9,241,801 B1 | 1/2016 | Parry et al. |
| 9,320,603 B2 | 4/2016 | Lieberman et al. |
| 9,408,699 B2 | 8/2016 | Stalcup et al. |
| 9,532,879 B2 | 1/2017 | Lieberman et al. |
| 9,901,451 B2 | 2/2018 | Conway et al. |
| 2004/0049285 A1 | 3/2004 | Haas |
| 2006/0025866 A1 | 2/2006 | Serafin et al. |
| 2008/0009874 A1 | 1/2008 | Meridew et al. |
| 2011/0015751 A1 | 1/2011 | Laird |
| 2013/0013077 A1 | 1/2013 | Metzger et al. |
| 2013/0020733 A1 | 1/2013 | Berger |
| 2014/0005791 A1 | 1/2014 | Bonitati et al. |
| 2014/0081408 A1 | 3/2014 | Lieberman et al. |
| 2014/0081410 A1 | 3/2014 | Lieberman et al. |
| 2014/0277528 A1 | 9/2014 | Mines et al. |
| 2014/0358242 A1 | 12/2014 | Mines |
| 2015/0335438 A1 | 11/2015 | Pierce et al. |
| 2016/0256280 A1 | 9/2016 | Trauner |
| 2017/0333211 A1 | 11/2017 | Flakne |

FOREIGN PATENT DOCUMENTS

| | | |
|---|---|---|
| FR | 2784577 A1 | 4/2000 |
| WO | 9730661 A1 | 8/1997 |
| WO | 2009049182 A1 | 4/2009 |
| WO | 2013006823 A1 | 1/2013 |

SPRING RETAINED FEMORAL AUGMENT

BACKGROUND OF THE INVENTION

Failure of a knee arthroplasty can be caused by a variety of factors, and such failure typically requires knee revision surgery. Oftentimes during revision procedures, a significant condylar defect requiring augmentation presents itself. When such condylar defect is present, the surgeon may correct this condition by preparing the defective bone to accept a joint implant that includes an augment. For example, a distal end of a femur may be resected to remove diseased or unhealthy bone which may be more significant on one condyle relative to the other, thus resulting in one resected condylar surface being distally offset relative to the other. To ensure establishment of the desired joint line and sufficient anchoring and proper fit of the femoral component implant, an augment is connected to a bone contacting side of the femoral component so as to fill in the space or spaces between the femoral component and the resected surface(s). In this regard, augments are typically used with a joint prosthesis to increase the thickness of the joint prosthesis at designated locations thereof in order to compensate for lack of sufficient bone tissue.

However, in order to determine the appropriate size augment, several augments may need to be assessed before the appropriate augment is discovered. Current augments can be connected to a joint prosthesis using a variety of means. However, such means currently available are either too time consuming to manipulate resulting in extended procedure times or do not sufficiently connected to the femoral component potentially resulting in a miscalculation and poor results. Thus, further improvements are desirable.

BRIEF SUMMARY OF THE INVENTION

In a first aspect of the present disclosure, an orthopedic system includes a first augment that has a body and a first biasing member projecting from the body. The body has a first and second face. The first and second faces are separated by a thickness of the augment. The system also includes a femoral prosthesis that has an articular side that defines condylar portions and a bone-facing side opposite the articular side. The bone facing side defines an augment opening sized to receive the augment therein. When the first augment is received within the augment opening, the first biasing member presses directly against the femoral prosthesis so as to retain the body within the augment opening.

Additionally, the augment opening may include an anterior slot and a posterior slot. The body may further include a main body portion and an end portion extending from the main body portion. The main body portion may have a thickness smaller than that of the end portion. The thickness of the first augment may be the thickness of the main body portion. The first biasing member may have a thickness equal to that of the end portion. The anterior and posterior slots may be configured to respectively receive the end portion and first biasing member.

Continuing with this aspect, the system may further include a second biasing member extending from the body. Each of the first and second biasing member may be a first and second springs. The first and second springs may be elliptical. The first and second springs may extend from the body such that they form a quarter ellipse. Each of the first and second biasing members may have first and second ends, the first end may be connected to the body and the second end may be a free end. The first and second biasing members may extend from the body and may curve in opposite directions such that the second ends of the first and second biasing members are positioned further apart from each other than the first ends of the biasing members. The system may also include a foot extending from the body. The first biasing member may extend at least partially about the foot. The system may further a second augment that has a body and a biasing member extending from the body. The second augment may have first and second faces that define a thickness therebetween. The thickness of the second augment may be greater than that of the first augment.

In another aspect of the present disclosure, a kit includes a plurality of augments. Each of the plurality of augments includes a body and a first biasing member projecting from the body. The body has a first and second face. The first and second faces are separated by a thickness of the augment. The kit also includes a femoral prosthesis that has an articular side that defines condylar portions and a bone-facing side opposite the articular side. The bone facing side defines an augment opening sized to receive each of the augments therein. When a first augment of the plurality of augments is received within the augment opening. The first biasing member presses directly against the femoral prosthesis so as to retain the body within the augment opening.

Additionally, the plurality of augments may have differing thicknesses that increase in 1 mm increments from one augment to the next. Also, the augment opening may include an anterior slot and a posterior slot. The body may further include a main body portion and an end portion extending from the main body portion. The main body portion may have a thickness smaller than that of the end portion. The thickness of the first augment may be the thickness of the main body portion. The first biasing member may have a thickness equal to that of the end portion. The anterior and posterior slots may be configured to respectively receive the end portion and first biasing member.

Continuing with this aspect, a second biasing member may extend from the body. Each of the first and second biasing members may have first and second ends. The first end may be connected to the body and the second end may be a free end. The first and second biasing members may extend from the body and curve in opposite directions such that the second ends of the first and second biasing members are positioned further apart from each other than the first ends of the biasing members. Also, each of the first and second biasing members may be a first and second springs. The first and second springs may be elliptical. The first and second springs may extend from the body such that they form a quarter ellipse. The kit may also include a foot that extends from the body. The first biasing member may extend at least partially about the foot.

In a further aspect of the present disclosure, a method of augmenting an implant includes providing a femoral prosthesis that has an articular side that defines condylar portions and a bone-facing side opposite the articular side. The bone facing side defines an augment opening sized to receive the augment therein. The method also includes inserting a first augment into the augment opening. The first augment has a body and a first biasing member projecting from the body. The body has a first and second face. The first and second faces are separated by a thickness of the augment.

Additionally, the step of inserting an augment into the augment opening may further include compressing the first biasing member. The first augment may be received within the augment opening. The first biasing member may press directly against the femoral prosthesis so as to retain the body within the augment opening. The method may further include removing the first augment from the augment opening, and inserting a second augment into the augment opening. The second augment may have a body and a biasing member extending from the body. The second augment may have first and second faces that define a thickness therebetween. The thickness of the second augment may be different than that of the first augment.

Also disclosed herein is the ornamental design or designs of an augment.

DETAILED DESCRIPTION

When referring to specific directions in the following discussion of certain implantable joint replacement devices, it should be understood that such directions are described with regard to the orientation and position of the implantable joint replacement devices during exemplary application to the human body. Thus, as used herein, the term "proximal" means situated nearer to the center of the body or the point of attachment and the term "distal" means more situated away from the center of the body or from the point of attachment. The term "anterior" means towards the front part of the body or the face and the term "posterior" means towards the back of the body. The term "medial" means toward the midline of the body and the term "lateral" means away from the midline of the body. Further, as used herein, the terms "about," "generally," and "substantially" are intended to mean deviations from absolute are included within the scope of the term so modified.

Figure 1A:
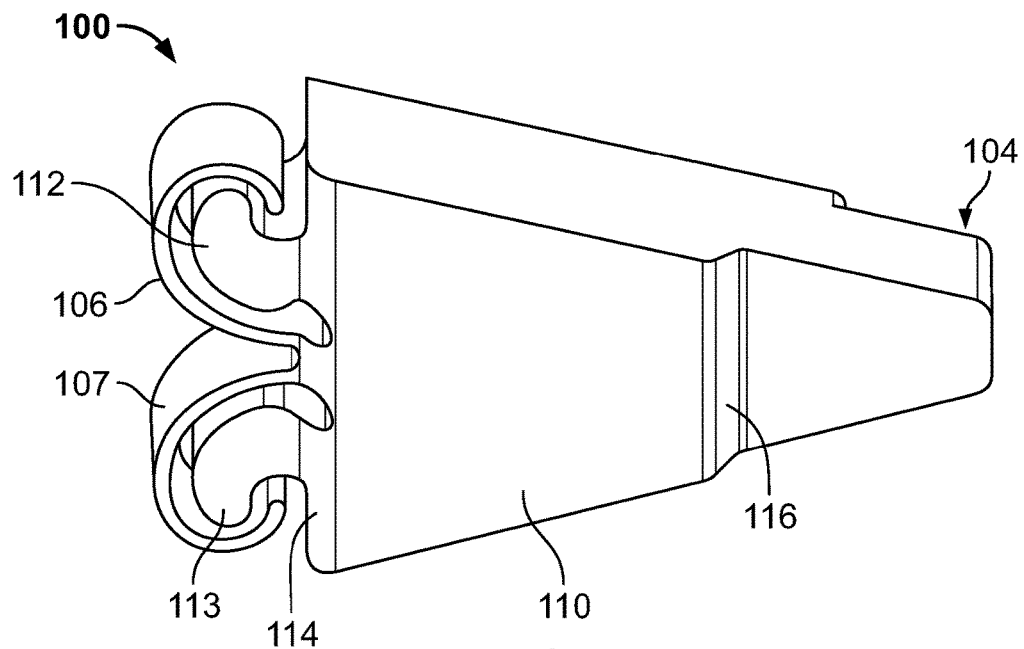
FIG. 1A is a bottom perspective view of an augment according to one embodiment of the present invention.
Figure 1B:
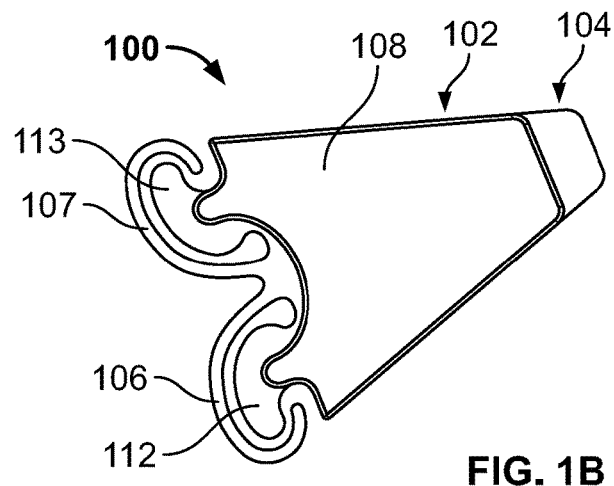
FIG. 1B is a top perspective view of the augment of FIG. 1.
Figure 1C:
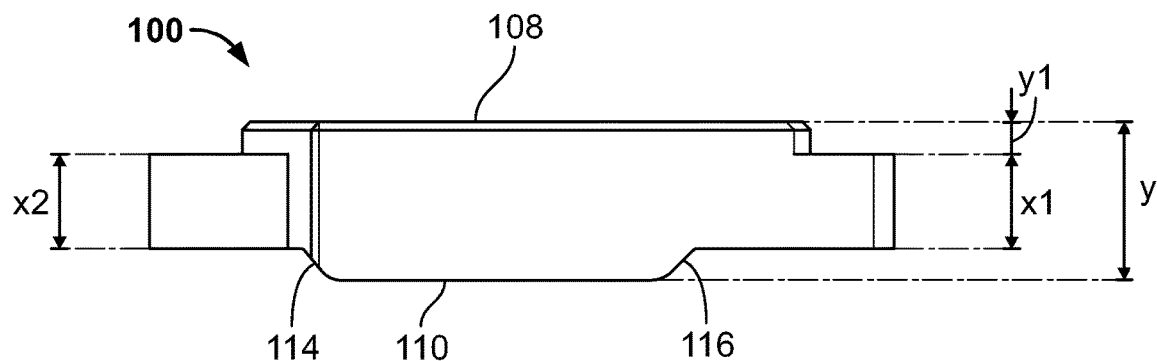
FIG. 1C is a side elevational view of the augment of FIG. 1.

Referring to FIGS. 1A-C, an augment is shown. Augment 100 has a body 102 that has a trapezoidal shape or truncated triangle shape. Alternatively, body 102 may have a different shape, such as rectangular, square, or the like. In this regard, augment 100 may have any shape that allows it to be received in an augment opening within a femoral prosthesis, as describe in more detail below.

Body 102 has a first face 108 and a second face 110 separated by a thickness "y." Projecting from a first end of the body 102 is an end portion 104. End portion 104 has a thickness "$x_1$" that is generally less than the thickness "y" of body 102, as best shown in FIG. 1C. However, in some embodiments, these thicknesses may be equal. Due to the difference in thicknesses between body 102 and end portion 104, an edge or shoulder 116 is formed between body 102 and end portion 104.

Augment 100 also includes, a plurality of biasing members 106, 107 that project from a second end of body 102. In the embodiment depicted, there are two biasing members 106, 107, which project from the second end of body 102. However, in other embodiments, augment 100 may have one biasing member or three or more biasing members. Biasing members 106, 107 have a thickness "$x_2$" that may be the same as thickness "$x_1$." Thus, thickness "$x_2$" of biasing members 106 may be less than thickness "y" of body 102. However, in other embodiments the thickness "$x_2$" of biasing members 106, 107 may differ from that of end portion 104.

Thickness "y" is preferably variable from one augment to another so that an operator can select the appropriate thickness augment to accommodate the particular patient. The portion of "y" that is variable is the dimension "y1" which is the distance between surface 108 and an upper surface of end portion 104. This dimension "y1" may increase from augment to augment in increments of 1 mm and determines how far out of augment opening 208 surface 108 projects. Thus, dimension "y1" generally dictates a nominal thickness of augment 100 such that an operator can determine the extent of a deficiency by the nominal thickness of augment 100 as dictated by the dimension "y1". Thus, where an augment 100 may have a thickness "y" of 3 mm, it may have a nominal thickness of 1 mm which would indicate a deficiency of 1 mm, for example. Moreover, an augment 100 that is neutral or of zero nominal thickness still has an overall thickness "y", but does not have a dimension "y1" that indicates a deficiency. In this regard, augments 100 may be and are preferably used to fill augment opening 208 so that surface contacts a resected bone surface of a bone that does not have a deficiency.

As shown, the biasing members 106, 107 are each in the form of a spring and extend from body 102 along an elliptical or curvilinear path so as to form a partial ellipse or quarter ellipse, and curve in opposite directions. Thus, biasing members 106, 107 have first ends attached to body 102 and second ends, which may be free ends, that are positioned further apart from each other than the first ends, as best shown in FIG. 1B.

Biasing members 106, 107 respectively curve around feet 112, 113. Feet 112, 113 are ridged features that extend from the second end of body 102 and that provide a backstop for and help prevent deformation of biasing members 106, 107. For example, feet 112, 113 are positioned adjacent to biasing members 106, 107 so as to prevent biasing members 106, 107 from being compressed towards body 102 so far that they plastically deform.

Augment 100, as shown, is monolithic. As such, body 102, end portion 104, biasing members 106, 107 and feet 112, 113 are all formed together as single, integral structure. Alternatively, Augment 100 may be made in separate pieces that are attached. For example, body 102 may be one piece and end portion 104 may be another that is at some point temporarily attached to end portion 104 using known means. Further, feet 112, 113 and biasing members 106 and 107 may also be separate pieces that are attached to body 102 using known means. As yet another alternative, any combination of body 102, end portion 104, biasing members 106, 107 and feet 112, 113 may be monolithic or in pieces that are to be attached to one another. Where augment 100 is monolithic, such monolithic structure can be made via an additive layer manufacturing ("ALM") process. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form the herein described implants, include stereolithography (SLA), fused deposition modeling (FDM), and continuous liquid interface production (CLIP).

Figure 2:
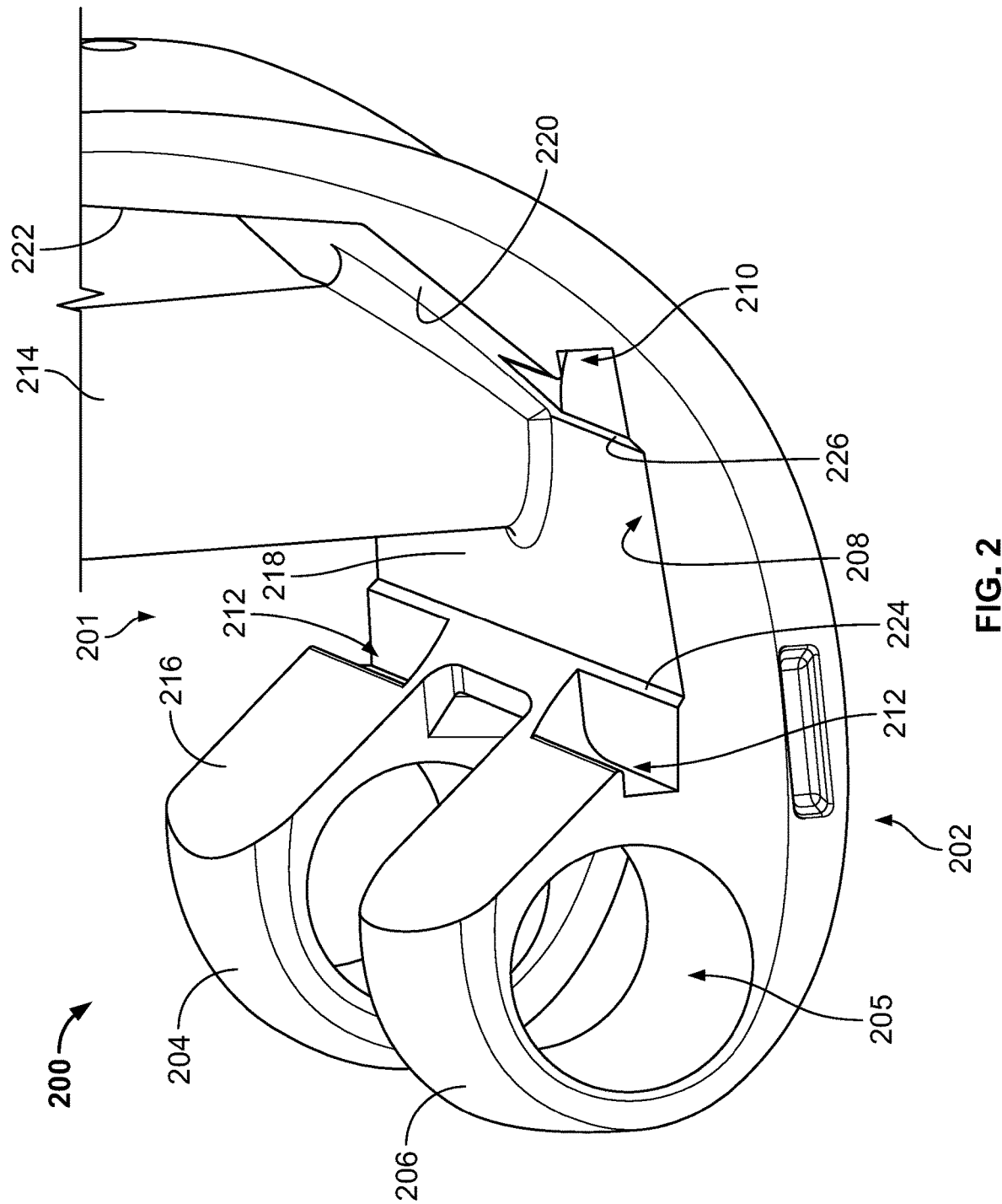
FIG. 2 is a side perspective view of a femoral component according to one embodiment of the present invention.

FIG. 2 illustrates an exemplary orthopedic implant, and in particular, a femoral implant 200 is shown. Implant 200, as shown, may be a hinged knee femoral component. However, implant 200 may be any femoral component used in a knee revision surgery. For Example, implant 200 may be a cruciate retaining, posterior stabilized, bi-cruciate retaining, or total stabilized femoral component.

Femoral implant 200 generally includes a bone contacting side 201, an articular side 202, a transverse opening 205 extending through femoral component 200 transverse to bone contacting and articular sides 201, 202, a pair of condylar portions 204, 206 and a stem portion or stem boss 214. As mentioned above, implant 200 is a hinge knee femoral component. In this regard, transverse opening 205 is configured to receive an axle about which a tibia flexes and extends. Such axle and other prosthetic hinge knee components that can be utilized in conjunction with femoral implant 200 can be found in U.S. Publication No. 2017/0035572, the disclosure of which is hereby incorporated herein by reference in its entirety.

The bone contacting side 201 includes inner surfaces 216, 218, 220, and 222 that are configured to face resected surfaces of a distal femur. Moreover, bone contacting side 201 defines an augment opening or recess 208 that extends along inner surface 218 to receive augment 100. Augment opening 208 includes at least one slot or groove, but preferably two slots/grooves at its anterior and/or posterior extents. For example, augment opening 208 has an anterior slot 210 and a posterior slot 212 as part of augment opening 208. Augment opening 208 extends along a horizontal axis or transverse axis of implant 200 such that each condylar portion 204, 206 has a posterior slot 212 and anterior slot 210 at the bone contacting side of implant 200 and so that slots 210 and 212 of condylar portions 204, 206 are at opposite sides of the stem boss 214. Thus, augment opening 208 is configured to receive an augment 100 on both the lateral and medial sides of implant 200 to account for lateral and/or medial bone deficiencies.

Inner surface 218 has a profile to match the profile of the second face 110 of augment 100. As such, inner surface 218 may have a female posterior edge or shoulder 224 that corresponds to a male posterior edge 114 of augment 100 as well as a female anterior edge 226 that corresponds to a male anterior edge 116 of augment 100. Such posterior and anterior edges 224, 226 are continuations of surfaces 216 and 220, respectively. However, edges 224 and 226 are formed by the intersection of posterior and anterior slots 212, 210 with recess 208, as shown in FIG. 2. Thus, the second face 110 of augment 100 may sit flush against inner surface 218 when augment 100 is received by augment opening 208 so that no gaps are present therebetween.

A kit may be provided to an operating room theater that includes femoral implant 200 and a plurality of augments 100. Augments 100 are universal such that they may fit right or left legged femoral implants and also may be received in augment opening 208 at either the medial or lateral sides of implant 200. In this regard, two augments 100 of the same thickness may be provided such that one can be connected to implant 200 at the medial side of implant 200 while the other can be connected to implant 200 at the lateral side of implant 200. Moreover, a plurality of different sized augments 100 may also be provided in the kit such that each of such differently sized augments 100 have incrementally different thicknesses. Such increments may be in 1 mm increments. Thus, for example, a kit may include pairs of augments 100 having nominal thicknesses of 0 mm, 1 mm, 2 mm, 3 mm, 4 mm, 5 mm, and 6 mm or any combination thereof.

Figure 3A:
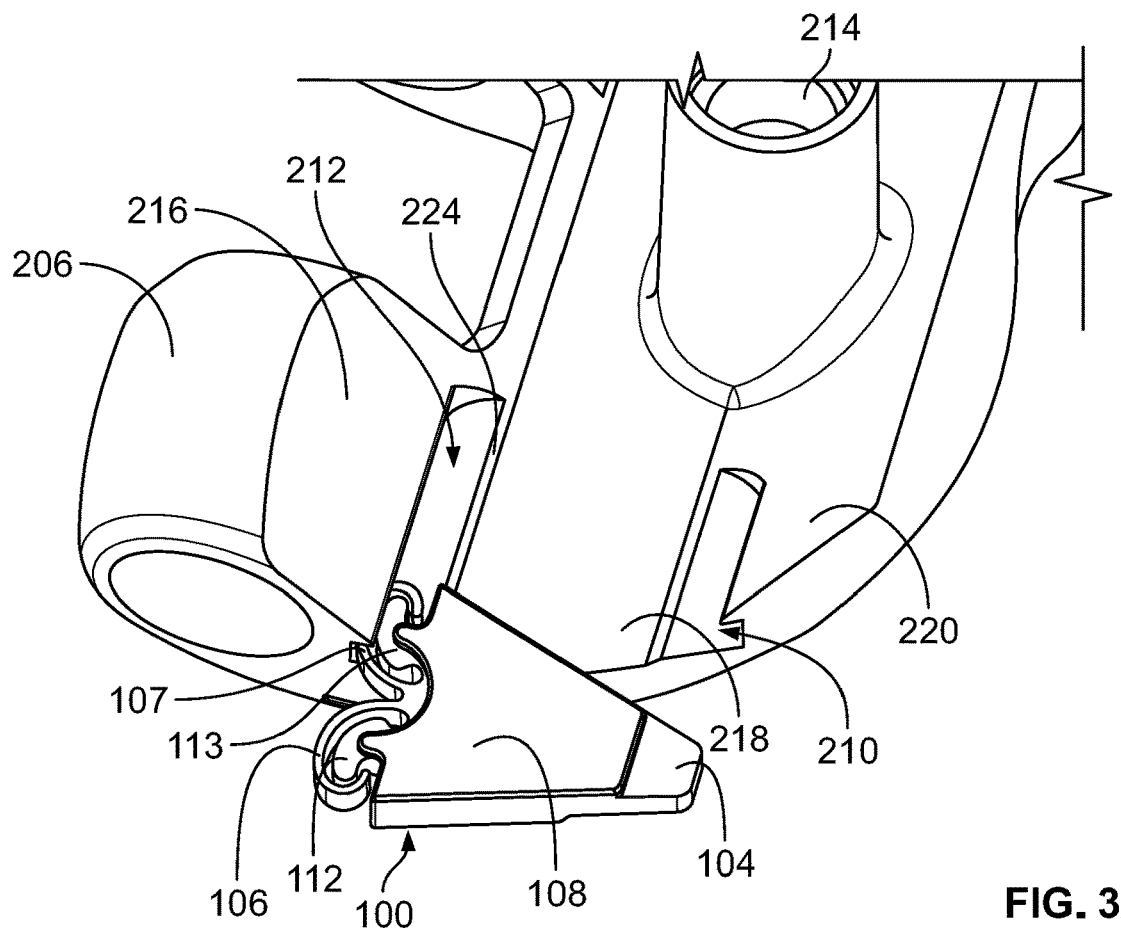
FIGS. 3A-D are perspective views of the augment of FIG. 1 being received by the femoral component of FIG. 2 according to one embodiment of the present invention.
Figure 3B:
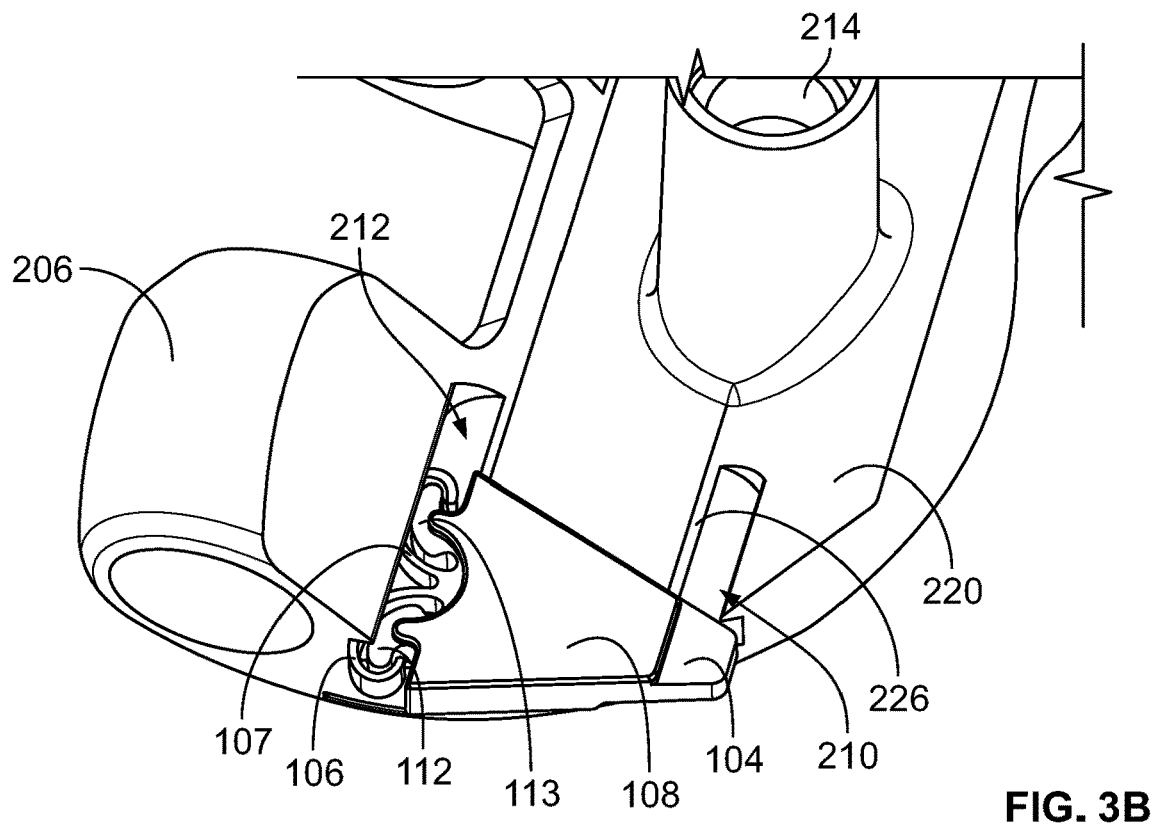
Figure 3C:
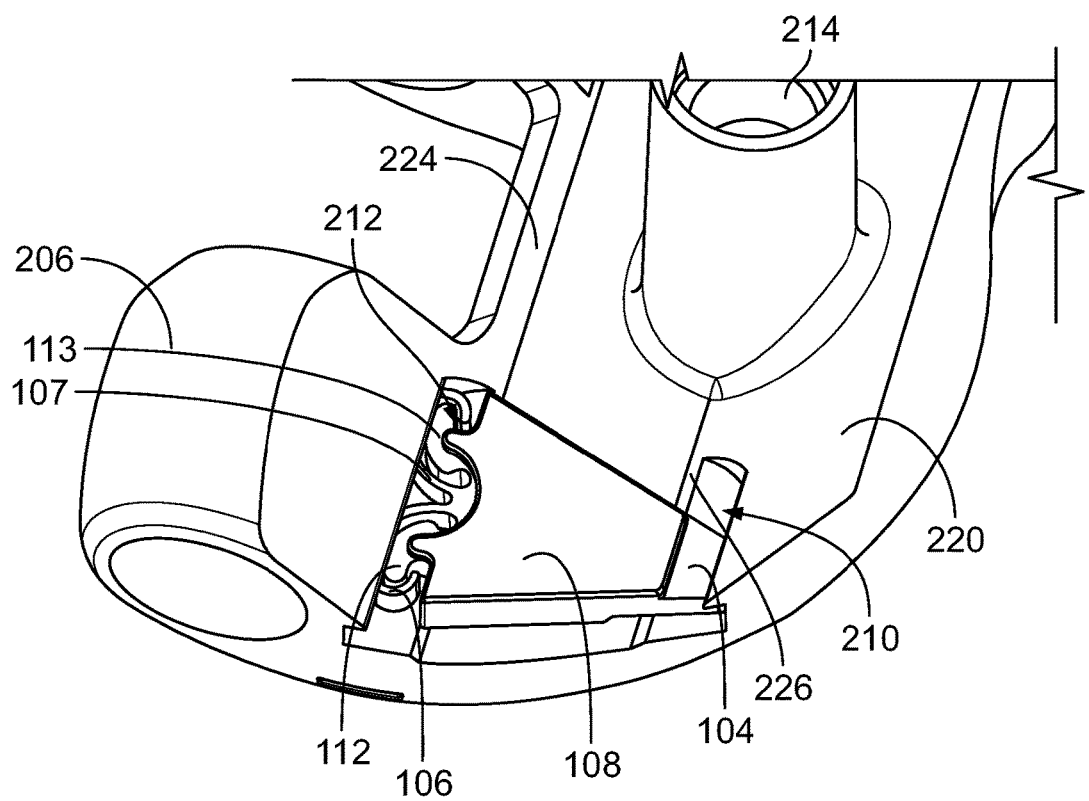
Figure 3D:
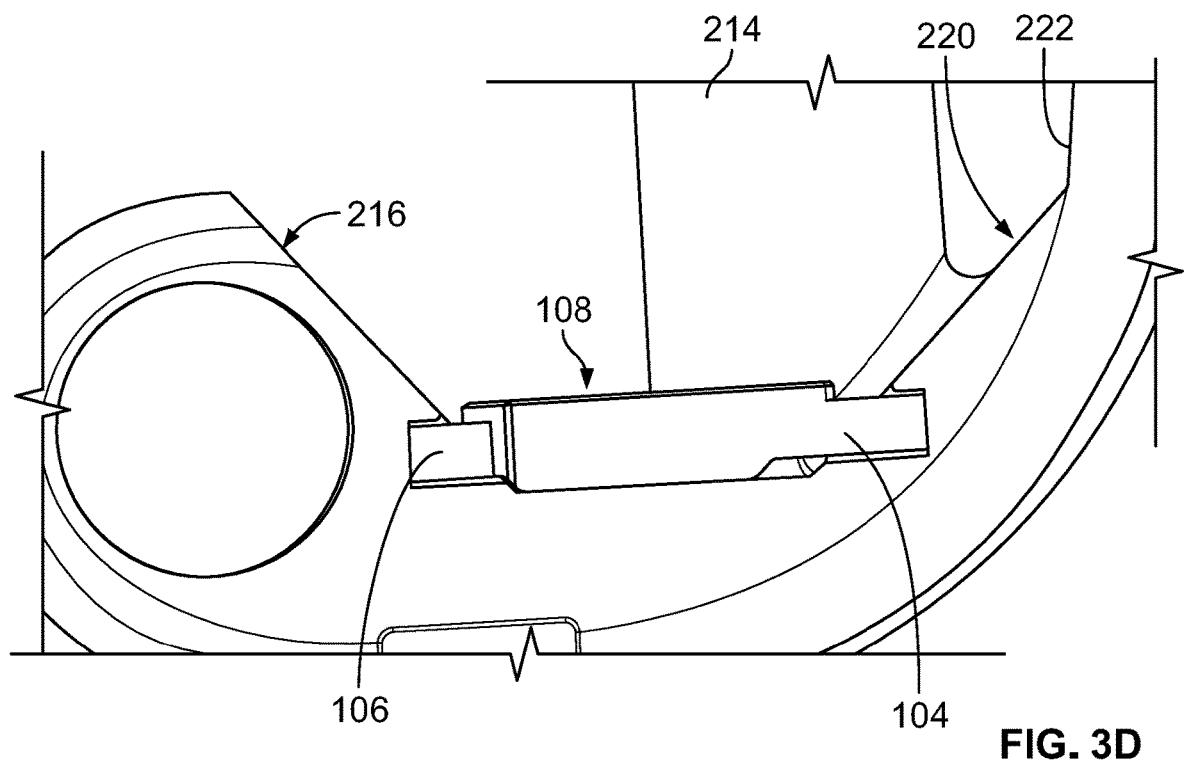
Figure 4:
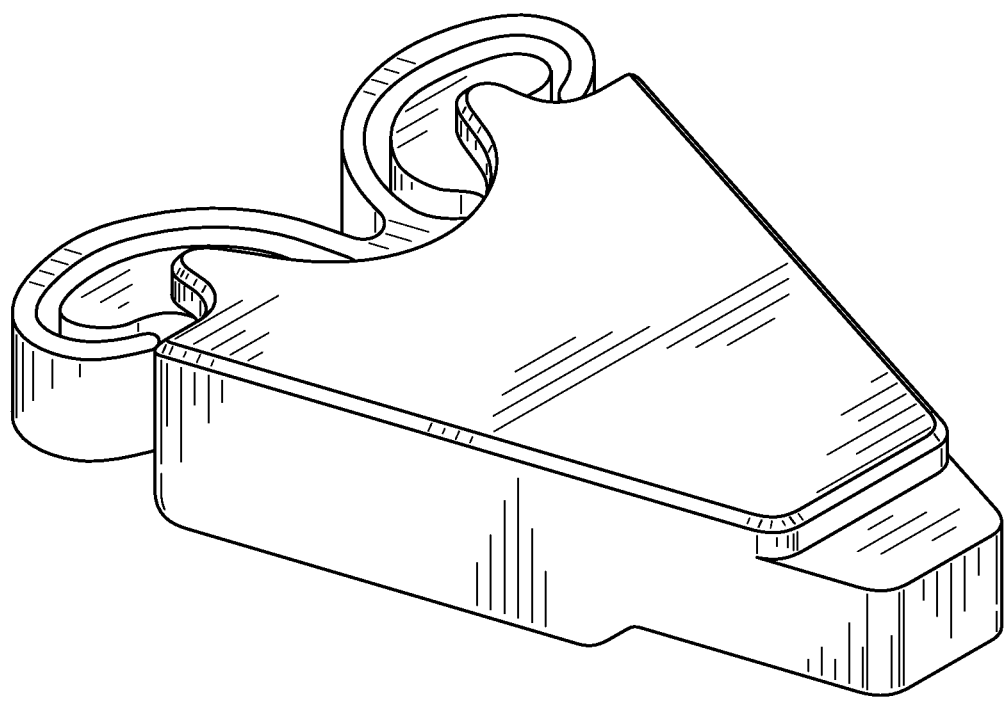
FIG. 4 is a top perspective view of an augment.
Figure 5:
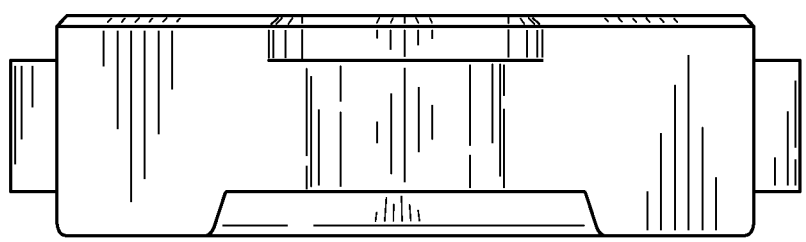
FIG. 5 is a right side elevational view of the augment of FIG. 4.
Figure 6:
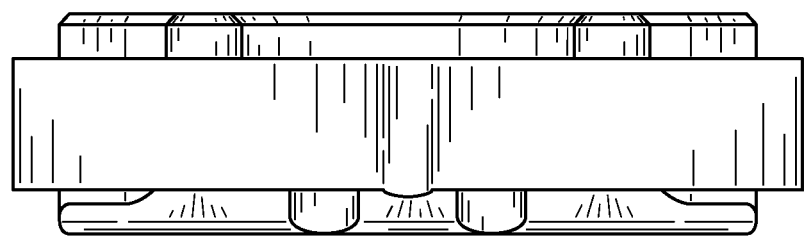
FIG. 6 is a left side elevational view of the augment of FIG. 4.
Figure 7:
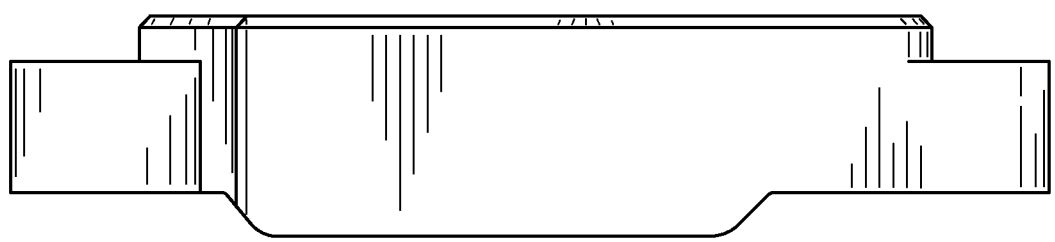
FIG. 7 is a front elevational view of the augment of FIG. 4.
Figure 8:
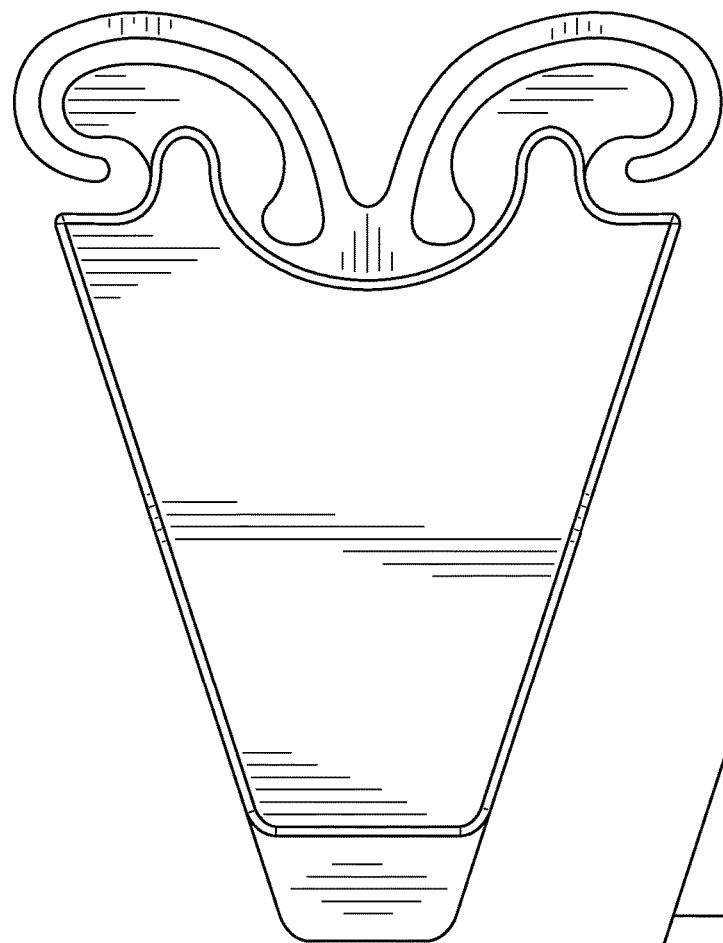
FIG. 8 is a top view of the augment of FIG. 4.
Figure 9:
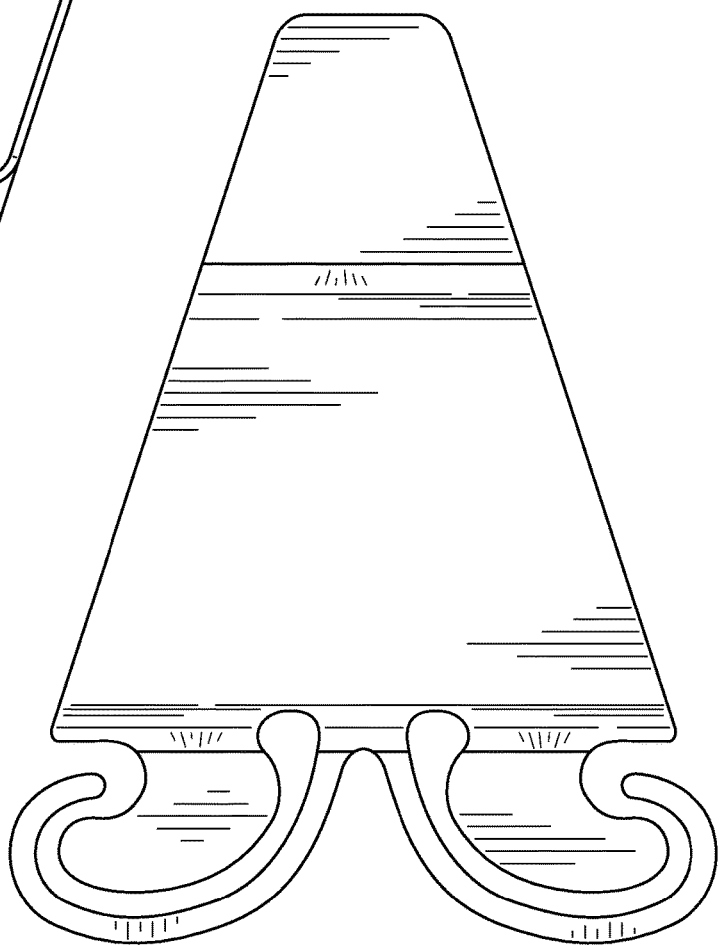
FIG. 9 is a bottom view of the augment of FIG. 4.

FIGS. 3A-D illustrate augment 100 being inserted into augment opening 208 of implant 200. Augment 100 may be aligned with augment opening 208 by aligning biasing members 106, 107 with posterior slot 212 and end portion 104 with anterior slot 210. Male posterior leading edge 114 of augment 100 may also be aligned with female posterior leading edge 224 of implant 200. Further, male central leading edge 116 of augment 100 may be aligned with female central leading edge 226 of implant 200. During alignment, only one of biasing members 106, 107 is inserted into posterior slot 212, as shown in FIG. 3A. Once augment 100 is aligned, it is pushed into opening 208.

Since the overall length of augment 100, including biasing members 106 and 107, may be greater than the overall anteroposterior width of opening 208, a compression force may be exerted on augment 100 in an anteroposterior direction via implant 200 as augment 100 is slid in a medial-lateral direction into opening 108. As the compression force is exerted on augment 100, biasing members 106, 107 compress from a first or equilibrium state to a second or biased state. During compression, biasing members 106, 107 move toward feet 112, 113 such that the space between biasing members 106, 107 and feet 112, 113 decreases. However, feet provide a limit to the distance biasing members 106, 107 can be compressed.

Once augment 100 is within augment opening 208, biasing members 106, 107 attempt to return to equilibrium from their biased or compressed state. For example, prior to the augment 100 being inserted into augment opening 208, biasing members 106, 107 are at the equilibrium state, i.e., biasing members 106, 107 are neither compressed nor stretched or expanded. Thus, when augment 100 is inserted into augment opening 208, biasing members 106, 107 are compressed as the longitudinal length of augment 100 in its equilibrium state is larger than the longitudinal length of augment opening 208. Therefore, for augment 100 to fit into augment opening 208, biasing members 106, 107 are compressed to the biased state to decrease the longitudinal length of augment 100 temporarily.

Upon insertion, however, biasing members 106, 107 attempt to return to their equilibrium state. This results in a biasing force exerted by biasing members 106, 107 on implant 200. Such biasing force secures augment 100 in augment opening 208 via friction until a lateral-medial force sufficient to overcome such friction is exerted on augment 100 to remove augment 100 from augment opening 208.

When augment 100 is fully inserted into augment opening 208, first face 108 of augment 100 becomes a bone contacting surface, particularly for a distal resected surface of a femur. In a knee arthroplasty procedure, if it is found that augment 100 does not adequately compensate for the deficiency, an augment with a larger thickness "y" may be swapped out with the augment 100 previously connected to implant 200. Thus, the first augment 100 may be removed from implant 200 and a second, larger, augment 100 is inserted into augment opening 208. This process may be repeated with various other augments of different thicknesses until a proper fit is determined. In addition, it should be understood that where a resected bone surface does not require augmentation, an augment 100 of nominal zero thickness is still inserted into implant 200 at the lateral and/or medial sides thereof so as to properly contact the resected, non-deficient bone surface.

Stated differently, a surgeon may be provided with a kit or surgical tray, such as the kit mentioned above, that includes a plurality of augments 100 as well as implant 200. A first augment may start with a nominal thickness of 2 mm for a bone surface known to be deficient. Such augment 100 is connected to implant 200, as described above. Implant 200 is then coupled to a resected femur and assessed for fit and function. If it is determined a thicker augment is needed, the first augment 100 is removed, which may be done without completely removing implant 200, by sliding augment 100 out of opening 208. Thereafter, a second augment 100 is slid into opening 208 and the fit and function is reassessed. This is repeated until the desired sized augment 100 is achieved. The augment size can then be translated into the selection of a permanent augment connected to a final femoral prosthesis.

While augment 100 and femoral component 200 may be used as a trial to assess an augment size for a final prosthesis where such augment may be connected to the final femoral component via a threaded fastener or the like, it is also contemplated that augment 100 and femoral component 200 can be used as final or permanent prostheses. In this regard, surface 108 may have a porous structure to facilitate bone ingrowth therein. Also, while the embodiment depicted herein is a femoral component and augment thereof, it should be understood that augment 100 may be used in conjunction with a tibial baseplate. In this regard, a tibial baseplate may have a lower bone contacting side with an opening and a pair of slots defining such opening that allows for the receipt of augment 100 or a similar augment with biasing members similar to members 106, 107.

Also disclosed herein is the ornamental design of augment 100. Such ornamental design is disclosed in FIGS. 4-9. It is noted that the ornamental design of the back view is identical to the front view. The applicant reserves the right to claim the ornamental design as shown and also with certain features disclaimed, such as chamfered surfaces, for example. In addition, the feet 112 and 113 and/or the springs 106 and 107 may be disclaimed from such claim or claims of the ornamental design.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic system comprising:
a first augment having a body and a first spring projecting from the body and being moveable relative to the body, the body having a first and second face, the first and second faces being separated by a thickness of the augment;
a femoral prosthesis having an articular side defining condylar portions and a bone-facing side opposite the articular side, the bone facing side defining an augment opening sized to receive the augment therein,
wherein, when the first augment is received within the augment opening, the first spring presses directly against the femoral prosthesis so as to retain the body within the augment opening; and further comprising a second spring extending from the body.

2. The system of claim 1, wherein the augment opening includes an anterior slot and a posterior slot.

3. The system of claim 2, wherein the body further includes a main body portion and an end portion extending from the main body portion, the main body portion having a thickness larger than that of the end portion, the thickness of the first augment being the thickness of the main body portion.

4. The system of claim 3, wherein the first spring has a thickness equal to that of the end portion.

5. The system of claim 3, wherein the anterior and posterior slots are configured to respectively receive the end portion and first spring.

6. The system of claim 1, wherein each of the first and second springs each have a first cross-sectional dimension greater than a second cross-sectional dimension extending perpendicular to the first cross-sectional dimension.

7. The system of claim 1, wherein the first and second springs are elliptical.

8. The system of claim 7, wherein the first and second springs extend from the body such that they form a quarter ellipse.

9. The system of claim 6, wherein each of the first and second springs have first and second ends, the first end being connected to the body and the second end being a free end.

10. The system of claim 9, wherein the first and second biasing springs extend from the body and curve in opposite directions such that the second ends of the first and second springs are positioned further apart from each other than the first ends of the springs.

11. The system of claim 1, further comprising a foot extending from the body, the first spring extending at least partially about the foot.

12. The system of claim 1, further comprising a second augment having a body and a spring extending from the body, the second augment having first and second faces defining a thickness therebetween, the thickness of the second augment being greater than that of the first augment.

13. A kit comprising:
a plurality of augments, each of the plurality of augments having a body and a first spring projecting from the body, the body having a first and second face, the first and second faces being separated by a thickness of the augment, the spring spring being moveable from a first state to a second state and biased toward the first state;
a femoral prosthesis having an articular side defining condylar portions and a bone-facing side opposite the articular side, the bone facing side defining an augment opening sized to receive an augment of the plurality of augments therein,
wherein, when a first augment of the plurality of augments is received within the augment opening, the first spring presses directly against the femoral prosthesis so as to retain the body within the augment opening; and further comprising a second spring extending from the body.

14. The kit of claim 13, wherein each of the first and second springs have first and second ends, the first end being connected to the body and the second end being a free end.

15. The kit of claim 14, wherein the first and second springs extend from the body and curve in opposite directions such that the second ends of the first and second springs are positioned further apart from each other than the first ends of the springs.

16. The kit of claim 13, wherein each of the first and second springs each have a first cross-sectional dimension greater than a second cross-sectional dimension extending perpendicular to the first cross-sectional dimension.

17. The kit of claim 16, wherein the first and second springs each extend along an elliptical path.

18. The kit of claim 13, further comprising a foot extending from the body, the first spring extending at least partially about the foot.

\* \* \* \* \*